United States Patent [19]

Scherlock et al.

[11] Patent Number: 5,023,265

[45] Date of Patent: Jun. 11, 1991

[54] SUBSTITUTED 1-H-PYRROLOPYRIDINE-3-CARBOXAMIDES

[75] Inventors: Margaret H. Scherlock, Bloomfield; Wing C. Tom, Cedar Grove, both of N.J.

[73] Assignee: Schering Corporation, Kenilworth, N.J.

[21] Appl. No.: 532,304

[22] Filed: Jun. 1, 1990

[51] Int. Cl.$^5$ .................. A61K 31/435; C07D 471/04
[52] U.S. Cl. ..................................... 514/300; 514/242; 514/253; 514/256; 544/182; 544/238; 544/333; 544/405; 546/113

[58] Field of Search ................ 546/113; 544/182, 238, 544/333, 405; 514/300, 242, 253, 256; 548/486

[56] References Cited

U.S. PATENT DOCUMENTS 3,634,453 1/1972 McManus et al. .................. 548/486
3,749,731 7/1973 Zinnes et al. ...................... 548/486

Primary Examiner—Bernard I. Dentz
Attorney, Agent, or Firm—James R. Nelson

[57] ABSTRACT

Substituted 1H-pyrrolopyridine-3-carboxamides and their use in pharmaceutical compositions and in treating inflammation are disclosed.

11 Claims, No Drawings

SUBSTITUTED 1-H-PYRROLOPYRIDINE-3-CARBOXAMIDES

BACKGROUND OF THE INVENTION

The present invention relates to novel substituted 1H-pyrrolo[2,3-b]pyridine-3-carboxamides having antiinflammatory activity and to pharmaceutical compositions and pharmacological methods employing such compounds.

Various 2-oxindole carboxamides are disclosed in the art. For example, U.S. Pat. No. 4,569,942 discloses certain 2-oxindole-1-carboxamide compounds having an acyl substituent at the 3-position as having analgesic and antiinflammatory activities. European published patent Application Nos. 0 181 136 and 0 173 520 disclose substituted 2-oxindole-3-carboxamides and tricyclic and quadracyclic compounds including the 2-oxindole-3-carboxamide unit as antiinflammatory agents. Various oxindole carboxamides have also been described in U.S. Pat. Nos. 3,634,453; 3,749,731; 4,686,224; and in European Patent Application Nos. 0 173 520; 0 164 860; 0 181 136; 0 137 163 and 0 156 603.

SUMMARY OF THE INVENTION

It has now surprisingly been found that compounds of formula I below have particularly advantageous properties useful in the treatment of inflammation:

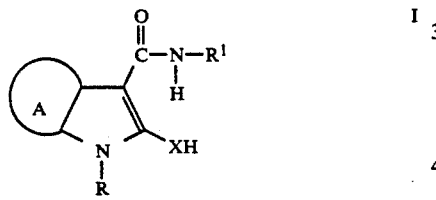

or a pharmaceutically acceptable salt or solvate thereof, wherein:
ring A represents a fused pyridine ring;
X is oxygen or sulfur; and
R represents hydrogen, alkyl, aryl, aralkyl, or a heterocyclic aromatic group.
$R^1$ represents alkyl, aryl, aralkyl, or a heterocyclic aromatic group.
Preferably, ring A represents

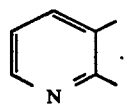

X is preferably O. $R^1$ preferably represents alkyl, phenyl, substituted phenyl, 2-, 3- or 4-pyridyl, 2- or 3-furyl, 2- or 3-thienyl, 2-, 4- or 5-thiazolyl, 2- or 4-imidazolyl, 3-oxazolyl or 5-methyl-3-oxazolyl. R preferably represents H, alkyl, phenyl or substituted phenyl. More preferably, R and $R^1$ each independently represents phenyl or substituted phenyl.

Preferred compounds of formula I include:

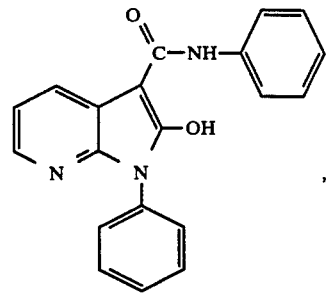

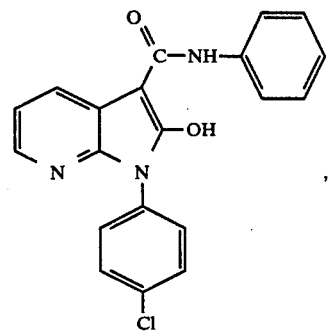

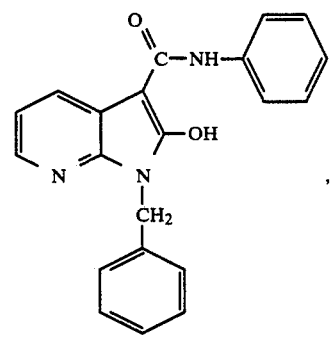

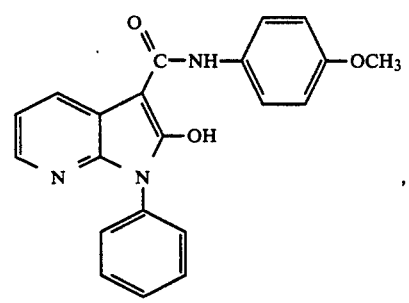

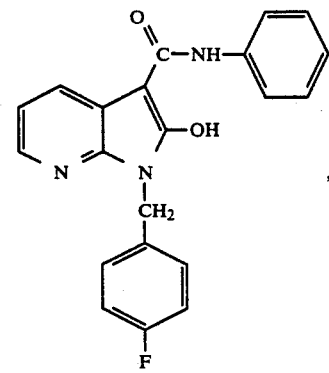

-continued

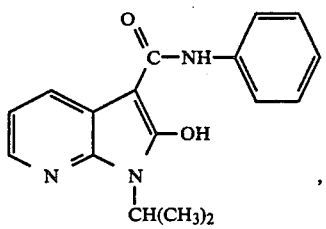

,

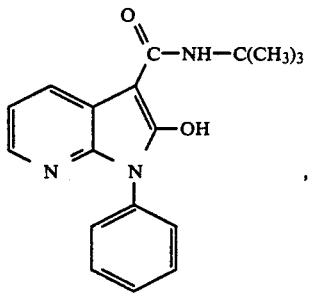

,

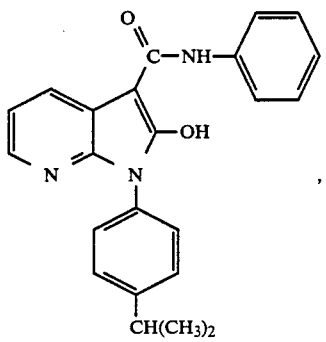

,

and

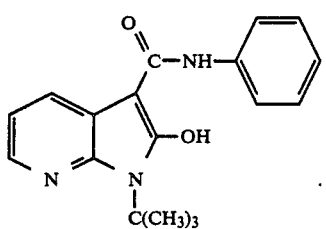

A particularly preferred compound is:

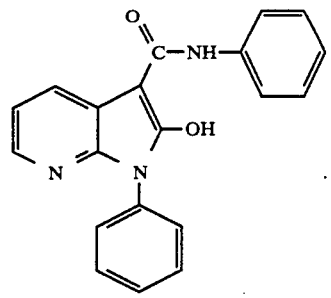

Other embodiments of the invention involve a pharmaceutical composition comprising a compound of formula I in combination with a pharmaceutically acceptable carrier and methods for treating inflammation in a mammal comprising administering to said mammal an effective amount of a compound of formula I for such purpose.

DETAILED DESCRIPTION OF THE INVENTION

Ring A is a fused pyridine ring, i.e., it has one of the following structures:

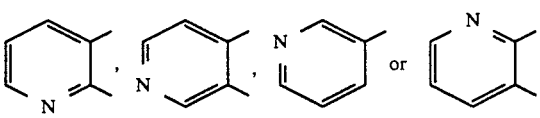

As mentioned above, ring A is preferably

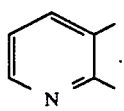

The compounds of the invention may exist in their keto or enolic forms. Thus, the compounds of formula I can exist in the form:

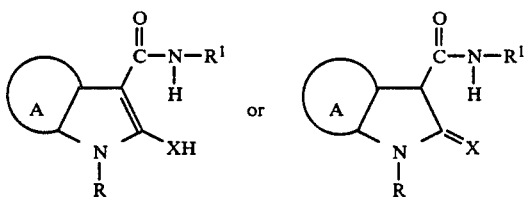

Certain compounds of the invention e.g., those with a basic group, also form pharmaceutically acceptable acid addition salts with organic and inorganic acids. Examples of suitable acids for such salt formation are hydrochloric, sulfuric, phosphoric, oxalic, malonic, salicylic, malic, fumaric, succinic, maleic, methanesulfonic and other mineral and carboxylic acids well known to those skilled in the art. The salts are prepared by contacting the free base form with a sufficient amount of the desired acid to produce a salt in the conventional manner. The neutralized forms may be regenerated by treating the salt with a suitable base solution such as sodium hydroxide, potassium carbonate, ammonia and sodium bicarbonate. The neutralized forms differ from their respective salt forms somewhat in certain physical properties, such as solubility in polar solvents, but the salts are otherwise equivalent to their respective neutralized forms for purposes of this invention.

Certain compounds of the invention will be acidic in nature, e.g., those compounds which possess an enolic group. These compounds may form pharmaceutically acceptable salts. Examples of such salts are the sodium, potassium, calcium, aluminum, gold, copper and silver salts.

As used herein, the terms below have the following meanings, unless otherwise indicated:

halo—represents fluoro, chloro, bromo or iodo;

alkyl (including the alkyl portions of aralkyl, alkoxy, etc.)—represents a straight or branched, saturated hydrocarbon chain having from 1 to 12, preferably from 1 to 6, carbon atoms, for example, methyl, ethyl, propyl, isopropyl, butyl, iso-butyl, tert-butyl, pentyl, hexyl and the like.

aryl (including the aryl portion of aralkyl)—represents phenyl, substituted phenyl, 1-naphthyl, 2-naphthyl and indanyl;

aralkyl—represents an alkyl group as defined above in which an aryl group as defined above is substituted for one of the alkyl hydrogen atoms;

substituted phenyl—represents a phenyl group in which 1 to 3 hydrogen atoms thereof are replaced by the same or different Y substituents each independently chosen from hydroxy, alkyl, halo, nitro, alkoxy, trifluoromethyl, cyano, cycloalkyl, SH, $S(O)_pR^a$ [wherein p is 0, 1 or 2 and $R^a$ is alkyl or phenyl];

cycloalkyl—represents a saturated carbocyclic ring having from 3 to 7 carbon atoms, for example cyclopropyl, cyclobutyl, cyclopentyl, cyclohexyl and the like;

alkoxy—represents an alkyl group covalently bonded to an adjacent structural element through an oxygen atom, such as for example, methoxy, ethoxy, n-propoxy, iso-propoxy, t-butoxy, n-pentoxy, n-hexoxy and the like; and heterocyclic aromatic group—represents a cyclic group having at least one O, S and/or N interrupting a carbocyclic ring structure and having a sufficient number of delocalized pi electrons to provide aromatic character, with the aromatic heterocyclic group having from 2 to 14, preferably from 2 to 6 carbon atoms, e.g., 2-, 3- or 4-pyridyl, 2- or 3-furyl, 2- or 3-thienyl, 2-, 4- or 5-thiazolyl, 2-, 4- or 5-imidazolyl, 2-, 4- or 5-pyrimidinyl, 2-pyrazinyl, 3- or 4-pyridazinyl, 3-, 5- or 6-[1,2,4-triazinyl], 3- or 5-[1,2,4-thiadizolyl], 2-, 3-, 4-, 5-, 6- or 7-benzofuranyl, 2-, 3-, 4-, 5-, 6- or 7-indolyl, 3-, 4- or 5-pyrazolyl, 2-, 4- or 5-oxazolyl, etc., in which the substitutable carbon atoms of the aromatic heterocyclic group may be substituted with a Y group as defined above. Preferred heterocyclic aromatic groups are 2-, 3- or 4-pyridyl, 2- or 3-furyl, 2- or 3-thienyl, 2- or 4-imidazolyl, 2-, 4-, or 5-thiazolyl, 3-oxazolyl or 5-methyl-3-oxazolyl.

The compounds of formula I may be prepared by general processes A, B and C described below, wherein R, $R^1$, X and ring A are as described above, unless otherwise indicated.

A. The compounds of formula I can be prepared by reacting a compound of formula III with a primary amine $R^1NH_2$:

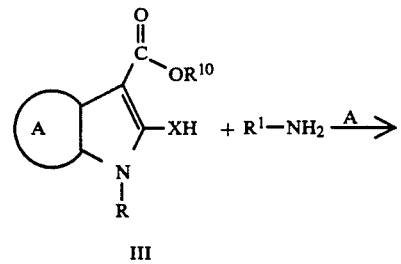

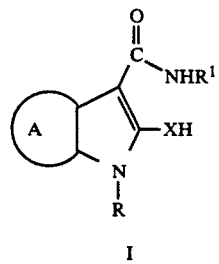

In the reaction A above, $R^{10}$ is an alkyl group such as an ethyl group. The reaction is typically performed at elevated temperature, e.g., from about 50° C. to reflux of the solvent. Any suitable solvent can be employed such as xylene, toluene, ethanol, etc. A catalytic amount of base such as triethylamine or sodium methoxide may optionally be included in the reaction mixture.

B. The compounds of formula I can also be prepared by reacting a compound of formula IV with an isocyanate $R^1NCO$:

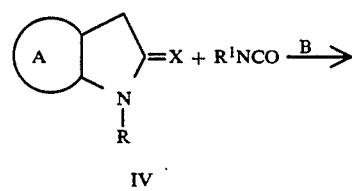

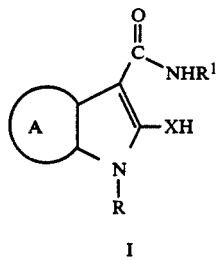

The reaction B above can be carried out in a suitable solvent such as dimethylformamide, tetrahydrofuran, or a non-polar hydrocarbon solvent, e.g., toluene, benzene or xylene. The reaction is preferably performed in the presence of a suitable base such as triethylamine, sodium hydride, butyl lithium, etc. Typically, the reaction is performed at temperatures of from about 0° C. to about 100° C., preferably from about room temperature to about 50° C.

C. Compounds of formula I can also be prepared by the following reaction:

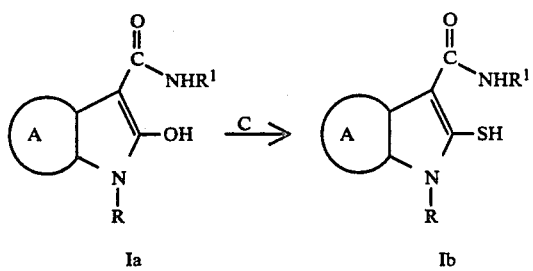

PREPARATIVE SCHEME III:

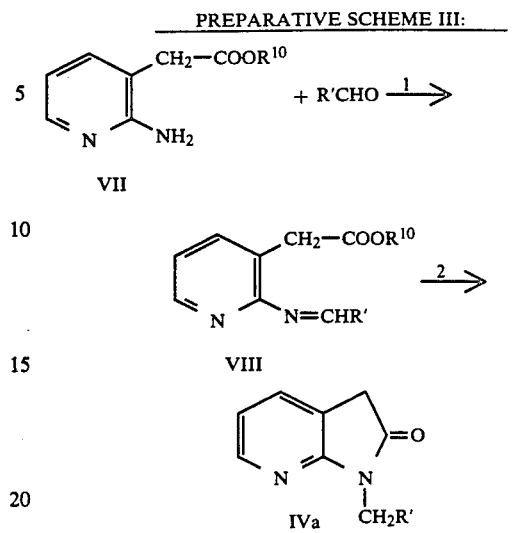

This exchange of sulfur for oxygen can possibly be carried out at an earlier stage in the preparation of the final compounds, e.g., in the preparation of some of the starting compounds III or IV. For example, the compounds of formulas IVa and IIIa below could be sulfurylated as described here. The replacement of oxygen by sulfur can be achieved by treatment with any suitable sulfurylating agent, e.g., Lawesson's reagent or $P_2S_5$ in a suitable solvent, e.g., toluene, benzene or xylene, at elevated (reflux) temperatures, e.g., 110° C. to 140° C.

The starting compounds III and IV used in the above processes A and B are either known or they may be prepared according to processes well-known in the art. Thus, for example, the starting compounds of formula III and IV may be prepared according to the following reaction schemes:

PREPARATIVE SCHEME I:

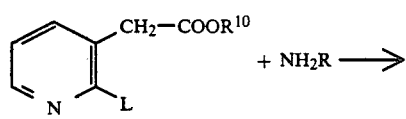

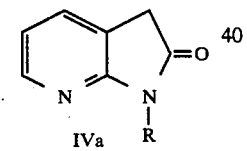

PREPARATIVE SCHEME II:

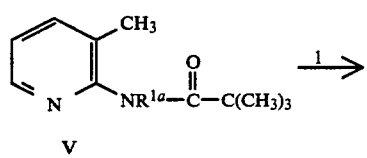

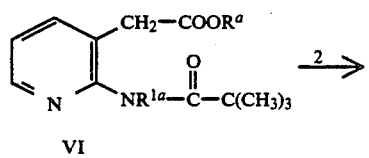

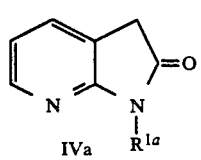

PREPARATIVE SCHEME IV:

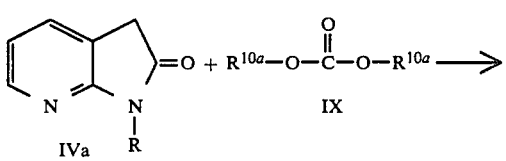

In Preparative Scheme I above, L represents a suitable leaving group such as chloro, bromo, mesyl, tosyl, etc. $R^{10}$ represents H or alkyl. This reaction is preferably performed in the presence of a catalytic amount of an acid such as paratoluenesulfonic acid, sulfuric acid, etc. The reaction can be run neat or in a suitable solvent such as an alcohol, e.g., pentanol, dimethylformamide, dioxane, etc.

In Step 1 of Preparative Scheme II above, the compound of formula V is reacted with a strong base such as n-butyllithium at a low temperature, such as from about −90° to 0° C. The base is present in amounts of from 2 equivalents or more. $R^{1a}$ and $R^a$ represent H or a metal such as lithium. Any suitable solvent may be employed, preferably an ether such as tetrahydrofuran, dioxane, diethylether, etc. Carbon dioxide is in contact with the reaction mixture at low temperatures as described below. A suitable acid, such as hydrochloric acid, is used in step 2 for the formation of formula IVa.

In Preparative Scheme III, $R^{10}$ of formula VII represents H or alkyl and R' represents an aryl group, so that in the final product R represents an R'—$CH_2$— group. The reaction step 1 is performed in the presence of a dehydrating agent such as molecular sieves, paratoluene sulfonic acid, sulfuric acid, etc. Typically, the reaction is run at temperatures of from about room temperature to the reflux temperature of the solvent employed. Suitable solvents include diethylether, benzene, toluene, etc.

In Step 2 of Preparative Scheme III, any suitable reducing agent such as sodium borohydride, borane dimethylamine complex, etc., or hydrogenation using a catalyst such as palladium on carbon in a suitable solvent may be employed. Suitable solvents for this reaction include, for example, ethanol, glacial acetic acid, etc. Typically, the reaction is performed at temperatures from about 20° C. to about 150° C.

In Preparative Scheme IV above, $R^{10a}$ represents an alkyl group such as methyl or ethyl. The reaction can be performed in a suitable solvent such as an alcohol, e.g., methanol, ethanol or pentanol, and in the presence of a strong base such as sodium methoxide or sodium ethoxide. Preferably, the reaction temperature is from about 60° C. to about 140° C.

The compound of formula IIIa or IVa may be converted to its thio analogue prior to its use in Processes A, B or C above. For example, the replacement of oxygen by sulfur can be achieved by treatment with any suitable sulfurylating agent, e.g. Lawesson's reagent or $P_2S_5$ as explained above.

The compounds of formula I inhibit the formation of both 5-lipoxygenase (5-LO) and cyclooxygenase (CO) derived products of arachidonic acid metabolism. The compounds of the invention may thus be used to treat rheumatoid arthritis, bursitis, tendonitis, gout and other inflammatory conditions.

The biological activity of classical nonsteroidal antiinflammatory drugs (NSAID) is attributable to inhibition of the cyclooxygenase pathway which converts arachidonic acid to prostaglandins. In diseases such as rheumatoid arthritis the NSAIDs do not alter the course of the disease and have GI side effects, as the cause of rheumatoid arthritis involves more than one mechanism. This hypothesis has been supported by the discovery of proinflammatory leukotrienes including a chemoattractant for neutrophils, leukotriene B4, which is formed from arachidionic acid via the 5-lipoxygenase pathway. A drug that inhibits both the cyclooxygenase and 5-lipoxygenase pathways may alter the course of the disease and lessen the side effects (such as the gastrointestinal effect) and therefore may be a superior antiinflammatory agent relative to one that inhibits only one of these pathways.

Anti-inflammatory activity of the compounds of the invention may be demonstrated by the Reversed Passive Arthus Reaction (RPAR) in the rat paw and in the rat pleural cavity, by the Adjuvant-Induced Arthritis in rats (AAR) assay, or/and by the Rat Cyclooxygenase-Lipoxygenase assay as described below:

Reversed Passive Arthus Reaction (RPAR) Assays

RPAR-Paw Assay

In order to determine the antiinflammatory activity by the reverse passive Arthus response, male Wistar-/Lewis inbred albino rats weighing 180-200 g were used. The rats were housed three animals per cage and fasted 24 hours prior to and during the study. Water was allowed ad libitum.

All reagents and drugs were prepared prior to the study. Crystallized and lyophilized bovine serum albumin (BSA) was solubilized in cold, sterile, pyrogen-free saline (PFS), 10 mg/mL. Lyophylized antibovine serum albumin (anti-BSA), the IgG fraction, was suspended or solubilized in an aqueous solution of methylcellulose (MC) with a homogenizer prior to administration.

One hour prior to sensitization with BSA, groups of animals (minimum six per group) were given drug in MC by gavage according to body weight (1.0 mL/100 g). Controls were given MC alone, and a drug standard, indomethacin, was usually included in each assay. Drugs were prepared so as to provide a dose for a 200 g animal, which was equivalent to the milligram per kilogram dose for the experiment. Each rat received an oral dose in a volume of approximately 2.0 mL. One hour after dosing, the animals were lightly anesthetized with ether and "sensitized" by injection into the penile vein with 0.2 mL of PFS containing 1 mg of BSA. One hour later, the animals were "challenged" in the right hind paw with subplantar injections of 0.2 mL PFS pyrogen-free salin containing 0.1 mg of anti-BSA bovine serum albumin. Immediately after the subplantar injections, the right hand paw was immersed (to the lateral maleolus) into the mercury well of a plethysmograph. The volume of mercury displaced was converted to weight and recorded. This value was considered to be the control reading for the animal. Paw volumes were also recorded with a plethysmograph during the development of the inflammation at 2 hours postchallenge.

Results were expressed by the change in paw volume from the control reading for each animal to that recorded 2 hours postchallenge. All drug-treated groups were compared to the MC control for significant differences by using analysis of variance (Duncan and Dunnetts). Differences from control in drug-treated groups were expressed as percent inhibition.

In order to determine the dose required to inhibit the inflammatory response by 50% ($ED_{50}$), a minimum of three and a maximum of five points were included in the assay. The $ED_{50}$ and the relative potency to a drug standard, indomethacin, were determined by linear regression analysis. (*J. Med. Chem.*, 1984, Vol. 27, No. 1, 27). Results for representative compounds of the invention are shown in Columns 3 and 4 of Table 1 below.

RPAR-Pleural Cavity Assay

Groups of 4 male rats were injected in the penile vein with antigen (1 mg BSA in 0.2 mL of saline per rat) and 0.5 hour later injected in the pleural cavity with antibody (1.0 mg antibody protein in the IgG fraction of rabbit anti-BSA in 0.2 mL). Sham control animals were treated as RPAR animals but did not receive BSA antigen. After 4 hours the animals were killed with $CO_2$, and the pleural cavities were opened and the exudate drained into a graduated conical glass centrifuge tube containing indomethacin (1.8 $\mu$g) and nordihydroguaiaretic acid (NDGA) (15 $\mu$g) to block ex vivo metabolite synthesis. The volume of the exudate was measured. The cavity was then washed out with saline-EDTA to achieve a final volume of 5.0 mL. The number of cells were determined in a Coulter Counter. The cells were spun-down (1000$\times$g) and the exudate supernatant was added to 4 volumes of 95% ethanol and samples were kept on ice for 30 minutes. After removal of the protein precipitate (2,500$\times$g) the ethanol extract of the exudate was dried under $N_2$ and then stored at $-20°$ C. For radioimmunoassay (RIA) analysis the samples were redissolved in water to a volume of 1 mL per rat. Utilizing internally spiked samples, recovery of $TXB_2$ (tritiated thromboxane $B_2$) and $LTE_4$ (tritiated leukotriene-$E_4$) from exudates was determined to be 84$\pm$2% (SEM) and 89$\pm$2% (N=4), respectively. Exudate samples were directly assayed in duplicate with the commercial $^3$H-TXB$_2$RIA kit from New England Nuclear and the $^3$H-LTC$_4$/D$_4$/E$_4$ kit from Amersham. The assay was validated using reversed-phase HPLC analysis of LTs in the standard procedure described by M. W. Musch, R. W. Bryant, C. Coscollaela, R. F. Myers and M. I. Siegel, Prostaglandins, Vol. 29, pp 405–430 (1985). Samples of ethanol exudate extract were "spiked" with $^3$H-LTs to follow HPLC purification and recovery.

Columns 5, 6, 7, 8 and 9 of Table 1 below shows the activity of a representative selection of compounds of formula I in this protocol.

Adjuvant-Induced Arthritis in Rats (AAR)

Heat-killed *Mycobacterium tuberculosis* (from the Ministry of Agriculture, Fisheries and Food Central Veterinary Laboratory, Weybridge, Surrey, England) was prepared by grinding to a fine powder. It was then weighed, mixed with paraffin oil (6 mg/mL) and homogenized.

The animals were dosed with drug 1 hour prior to challenge with adjuvant and then for 21 consecutive days. Control animals were given methyl cellulose. Injection of 0.1 mL of the adjuvant was made into the left hind paw. The left and right hind paw volumes were measured immediately on a plethysmograph. Final measurements were taken on both paws on day 21 of the assay. Data were reported as Δ paw volume. (Watnick, A. S., *Monogr. Physiol. Soc.*, Phila. 1975, 1, 155–171).

Results with representative compounds of the invention are shown in column 13 of Table 1 below.

Rat CO/LO Inhibition

Male Wistar-Lewis rats were injected iv with 5 mg of BSA in 0.2 mL of pyrogen-free saline followed by an intrapleural injection of 500 μg of the IgG fraction of rabbit anti-BSA in 0.2 mL of pyrogen-free saline, all under light anesthesia. After 4 hours the pleural cavity exudate, consisting of 85–95% neutrophils, was removed. Neutrophils were isolated from the pleural exudates by centrifugation at 4° C. for 10 minutes at 200 g. The cell pellet was briefly resuspended in 17 mM Tris-HCl buffer, pH 7.2, containing 0.75% NH$_4$Cl in order to lyse red cells, followed by centrifugation at 4° C. for 5 minutes at 200 g. The pelleted neutrophils were rewashed in 50 mM Tris-HCl, pH 7.4, containing 100 mM NaCl and 1 mM CaCl$_2$, for a final cell count of approximately $5 \times 10^6$ intact neutrophils/0.1 mL of suspension.

Arachidonic acid metabolism via cyclooxygenase and 5-lipoxygenase was determined by preincubating the above cell suspension with the test compound for 4 minutes at room temperature and then adding 0.1 mL of the preincubated cells to assay tubes. The final assay mixture (0.1 mL) contained 40 μM [1-$^{14}$C]arachidonic acid, 10 μM calcium A$_{23187}$ ionophore and 0.1% BRIJ ®56 detergent. After 1 minutes at 37° C., assays were terminated by the addition of 2.4 mL of a CHCl$_3$/CH$_3$OH (1:1 v/v) mixture and 0.9 mL of 0.1% HCOOH. The suspension was vortexed, immediately cooled on ice, and centrifuged and the organic layer withdrawn. The extract was evaporated and resuspended in 0.1 mL of CHCl$_3$/CH$_3$OH (1:2, v/v) for spotting on silica gel TLC plates (without gypsum). Development was with petroleum ether/diethylether/acetic acid (40:60:1, v/v/v). Products were located by autoradiography and the appropriate regions scraped and counted in a liquid scintillation counter. The 5-lipoxygenase metabolite 5-hydroxy-6,8,11,14-eicosatetraenoic acid (5-HETE) and the cyclooxygenase metabolite 12-hydroxy-hepta-5,8,10-trienoic acid (HHT) were identified by cochromatography with authentic standards on TLC plates. Results are reported as percent inhibition of cyclooxygenase and lipoxygenase metabolite formation. (Myers, R. F.; Siegel, M. I., *Biochem. Biophys. Res. Commun.*, 1983, 112, 586.) Results with representative compounds of the invention are shown in Columns 10, 11 and 12 of Table 1 below.

TABLE 1

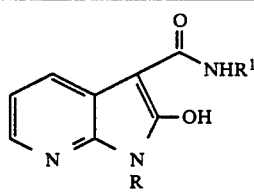

| R | R$^1$ | RPAR-Paw Dose mg/kg | RPAR-Paw % Inhib. | RPAR-Pleural Cavity Dose mg/kg | RPAR-Pleural Cavity % Inhibition Cells | RPAR-Pleural Cavity % Inhibition Fluid | RPAR-Pleural Cavity % Inhibition TXB$_2$ | RPAR-Pleural Cavity % Inhibition LTE$_4$ | Cyclooxygenese/lipoxygenese Dose M × 10$^{-5}$ | Cyclooxygenese/lipoxygenese % Inhib. HHT | Cyclooxygenese/lipoxygenese % Inhib. 5-HETE | AAR ED50 mg/kg |
|---|---|---|---|---|---|---|---|---|---|---|---|---|
| phenyl | phenyl | 25 | 60 | 25 | 56 | 49 | — | — | 5 | 93 | 34 | 9 |
|  |  |  |  | 50 | 61 | 27 | 100 | 59 |  |  |  |  |
| 3-CF$_3$-phenyl | phenyl | 50 | 60 | 25 | 0 | 0 | — | — | 5 | 56 | 35 | — |

TABLE 1-continued

[Structure: pyrrolo-pyridine with C(=O)NHR¹ and OH substituents, N-R]

| | | RPAR-Paw | | RPAR-Pleural Cavity | | | | Cyclooxygenese/lipoxygenese | | | AAR |
|---|---|---|---|---|---|---|---|---|---|---|---|
| | | Dose | % | Dose | % Inhibition | | | Dose | % Inhib. | | ED50 |
| R | R¹ | mg/kg | Inhib. | mg/kg | Cells | Fluid | $TXB_2$ | $LTE_4$ | $M \times 10^{-5}$ | HHT | 5-HETE | mg/kg |
| C(CH₃)₃ | phenyl | 25 | 36 | 25 | 41 | 26 | — | — | — | — | — | — |
| phenyl | 2-pyridyl | 50 | 26 | — | — | — | — | — | 5 | 78 | 2 | — |
| 4-Cl-phenyl | phenyl | 50 | 56 | 25 | 51 | 18 | — | — | 5 | 96 | 20 | — |
| phenyl | 3-CF₃-phenyl | 25 | 41 | 25 | 22 | 0 | — | — | 5 | 60 | 18 | — |
| phenyl | 2,4-F₂-phenyl | 50 | 33 | — | — | — | — | — | 5 | 96 | 19 | — |
| CH₂-phenyl | phenyl | 25 | 42 | 25 | 36 | 76 | — | — | 5 | 34 | 35 | 33 |
| phenyl | 3-methyl-4-methylisoxazole | 25 | 10 | 25 | 0 | 0 | — | — | 5 | 45 | 22 | — |
| H | phenyl | 25 | 22 | — | — | — | — | — | 5 | 0 | 9 | — |

TABLE 1-continued

[Structure: pyridine fused with pyrrole, bearing C(=O)NHR¹ at 3-position, OH at 2-position, R on pyrrole N]

| R | R¹ | RPAR-Paw Dose mg/kg | RPAR-Paw % Inhib. | Dose mg/kg | RPAR-Pleural Cavity % Inhibition | | | | Cyclooxygenese/ lipoxygenese Dose M × 10⁻⁵ | % Inhib. HHT | % Inhib. 5-HETE | AAR ED50 mg/kg |
|---|---|---|---|---|---|---|---|---|---|---|---|---|
| | | | | | Cells | Fluid | TXB₂ | LTE₄ | | | | |
| phenyl | 4-OCH₃-phenyl | 25 | 42 | 25 | 28 | 27 | — | — | 1.5 | — | 9 | — |
| phenyl | (CH₂)₃CH₃ | 25 | 29 | 25 | 19 | 0 | — | — | 5 | 44 | 2 | — |
| phenyl | CH₂-phenyl | 25 | 0 | 25 | 0 | 0 | — | — | 5 | 34 | 0 | — |
| CH₂-(4-F-phenyl) | phenyl | 25 | 32 | 25 | 30 | 46 | — | — | 5 | 57 | 17 | — |
| CH(CH₃)₂ | phenyl | — | — | 25 | 34 | 44 | — | — | — | — | — | — |
|  |  |  |  | 50 | 65 | 57 | — | — | — | — | — | — |
| phenyl | 2-OH-5-COOH-phenyl | 25 | 4 | 25 | 0 | 0 | — | — | — | — | — | — |
| phenyl | C(CH₃)₃ | 25 | 49 | 25 | 66 | 23 | — | — | — | — | — | — |
| 4-CH(CH₃)₂-phenyl | phenyl | 25 | 34 | 25 | 9 | 8 | — | — | — | — | — | — |

TABLE 1-continued

| | | RPAR-Paw | | Dose mg/kg | RPAR-Pleural Cavity % Inhibition | | | | Cyclooxygenese/ lipoxygenese | | | AAR ED50 mg/kg |
|---|---|---|---|---|---|---|---|---|---|---|---|---|
| | | Dose mg/kg | % Inhib. | | Cells | Fluid | TXB$_2$ | LTE$_4$ | Dose M × 10$^{-5}$ | % Inhib. 5-HHT | HETE | |
| R | R$^1$ | | | | | | | | | | | |
| \|<br>CH$_3$ | [phenyl] | — | — | 25 | 45 | 5 | — | — | 5 | 0 | 0 | — |

The compounds of formula I can be administered in any number of conventional dosage forms. Solid dosage forms include capsules, tablets, pills, powders, suspensions, solutions, cachets or suppositories. Parenteral preparations include sterile solutions or suspensions. Inhalation administration can be in the form of a nasal or oral spray, or by insufflation. Topical dosage forms can be creams, ointments, lotions, trasdermal devices (e.g., of the conventional patch or matrix type) and the like.

The formulations and pharmaceutical compositions contemplated by the above dosage forms can be prepared with conventional pharmaceutically acceptable excipients and additives, using conventional techniques. Such pharmaceutically acceptable excipients and additives are intended to include carriers, binders, flavorings, buffers, thickeners, color agents, stabilizing agents, perfumes, preservatives, lubricants, etc.

When used orally or parenterally for the treatment of inflammation, the compounds of the invention can be administered in an amount ranging from about 0.1 mg/kg to about 100 mg/kg, preferably from 0.1 mg/kg to about 50 mg/kg per day. Determination of the proper dosage of a compound of the invention for a particular situation is within the skill of the art. Generally, treatment is initiated with smaller dosages which are less than the optimum doses of the compound. Thereafter, the dosage is increased by small increments until the optimum effect under the circumstances is reached. For convenience, the total daily dosage may be divided and administered in portions during the day if required.

The amount and frequency of administration of the compounds of formula I and the pharmaceutically acceptable salts thereof will be regulated according to the judgment of the attending clinician considering such factors as age, condition and size of patient as well as severity of the symptom being treated. A typical recommended dosage regiment is oral administration of from 10 mg to 1500 mg/day preferably 10 to 750 mg/day, in two to four divided doses to achieve relief of the inflammation symptoms.

The following examples are intended to illustrate, but not to limit, the present invention.

PREPARATIVE EXAMPLE 1

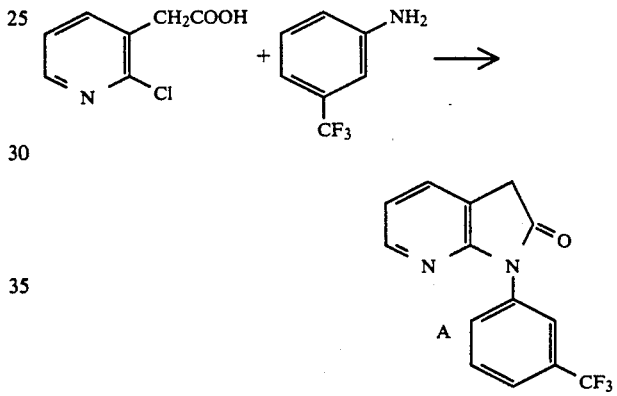

A stirred mixture of 5 grams(g) (0.029 mole) of 2-chloro-3-pyridineacetic acid, 9.4 g (0.058 mole) of 3-trifluoromethylaniline and 50 mg of p-toluenesulfonic acid in 15 mL of n-pentanol is heated for 24 hours from 130° to 140° C. After the solvent is removed at reduced pressure, the resulting solid residue is triturated with water, filtered, and recrystallized from isopropylacetate to afford 6 g of pure product of Formula A with melting point 133°–134° C. (75% yield). By essentially the same method using aniline, 1,3-dihydro-1-phenyl-2H-pyrrolo[2,3-b]pyridine-2-one is prepared, m.p. 120°–121° C.

PREPARATIVE EXAMPLE 2

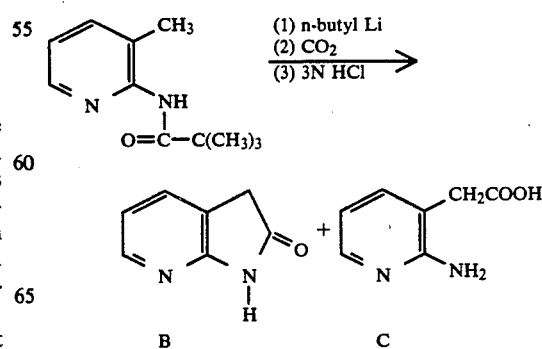

To a stirred solution of 96 g (0.5 mole) of 2-(trimethylacetylamino)-3-methylpyridine in 1500 mL of dry tetrahydrofuran at −10° C. is added 423 mL of 2.6M n-butyllithium-hexane solution dropwise over one hour. The mixture is maintained at −5° to 0° C. for 4 hours and then poured into a stirred suspension of 1.5 kg of dry ice powder in 700 mL of diethyl ether. Solvent is removed at reduced pressure and the resulting solid residue mixed with 1200 mL of 3N hydrochloric acid, and refluxed for 4 hours. 1000 mL of water are removed at reduced pressure and the remaining solution is neutralized with 10% NH₄OH. The precipitated 2-amino-3-pyridineacetic acid (33 g, m.p. 232°–235° C.) is collected by filtration. Subsequent extraction of the filtrate with methylene chloride affords 19 g of the compound of Formula B, m.p. 177°–179° C.

PREPARATIVE EXAMPLE 3

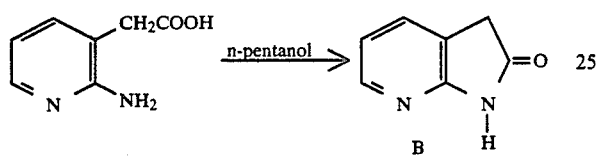

A suspension of 4 g (26.3 mmole) of 2-amino-3-pyridineacetic acid and 35 mg of p-toluenesulfonic acid in 18 mL of n-pentanol is refluxed for 2 days. The mixture is concentrated at reduced pressure to a solid, which is recrystallized with methylene chloride-petroleum ether affording 2 g of pure product of Formula B.

PREPARATIVE EXAMPLE 4

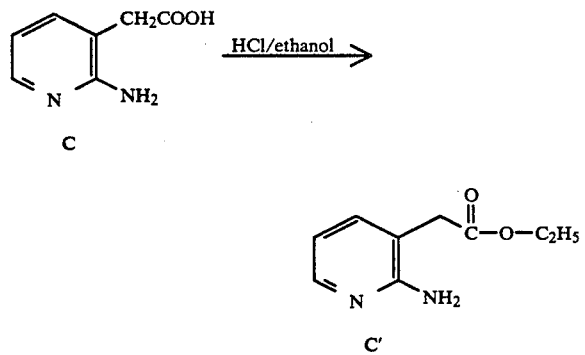

A suspension of 15 g (0.099 mole) of 2-amino-3-pyridineacetic acid (Formula C) in 250 mL of ethanol and 60 mL of 12% HCl—C₂H₅OH solution is refluxed for 0.5 hours. The precipitant and hydrogen chloride salt of the product (m.p. 188°–190° C.) is filtered (14.3 g), dissolved in cold methylene chloride (100 mL) and 7 mL of triethylamine and washed with cold water. The organic solution is dried over anhydrous magnesium sulfate (MgSO₄) and concentrated at reduced pressure to an oil of Formula C' above (11 g, free base of the product).

PREPARATIVE EXAMPLE 5

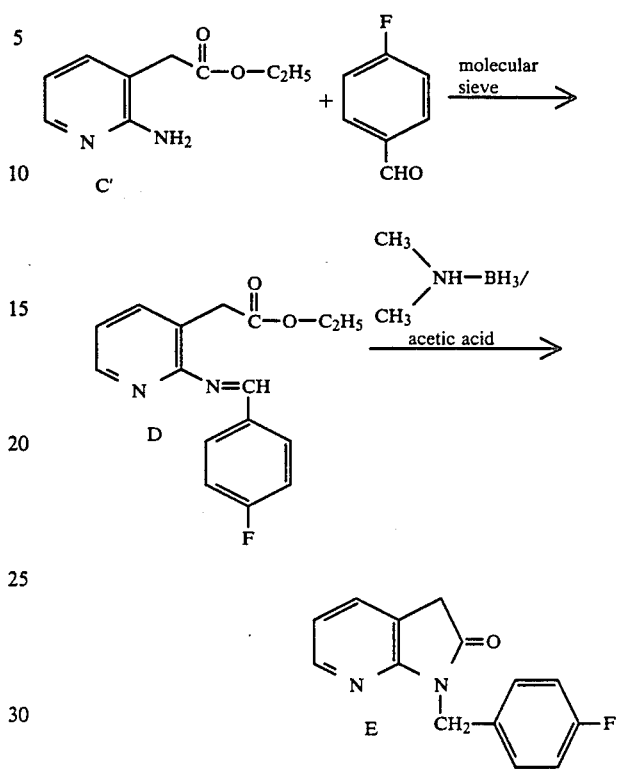

To a stirred suspension of 15 g (0.069 mole) of ethyl 2-amino-3-pyridineacetate hydrochloride (Formula C') in 50 mL of methylene chloride is added 10 mL of triethylamine, followed 8.83 g (0.069 mole) of 97 percent 4-fluorobenzylaldehyde, 120 g of 5 Å molecular sieve, and 200 mL of toluene. Stirring is maintained for 20 hours. The reaction mixture is filtered and the filtrate is concentrated at reduced pressure to an oil which is distilled and collected to yield a compound of Formula D above, b.p. 155°–160°/0.07 mm, 11.5 g.

To 4.6 g (0.016 mole) of the compound of Formula D above in 15 mL of glacial acetic acid is added 0.47 g (0.008 mole) of boran dimethylamine in 10 mL of glacial acetic acid in one portion. The mixture is refluxed for 1 hr, cooled and diluted with water. The precipitated product is filtred and recrystallized with isopropyl ether to yield 2.7 g of a compound of Formula E, m.p. 120°–121° C.

PREPARATIVE EXAMPLE 6

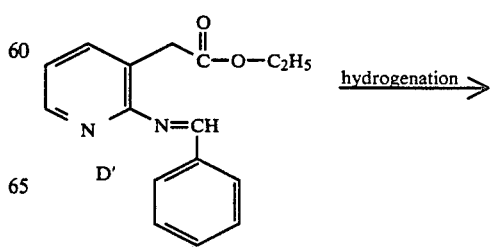

-continued

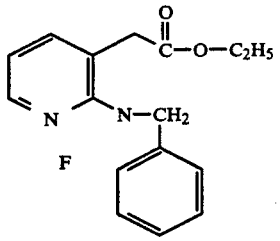

A solution of 38.4 g (0.143 mole) of ethyl 2-(benzylideneimino)-3-pyridineacetate (Formula D', which was prepared essentially as described in Preparative Example 5 above by substituting benzaldehyde in place of 4-fluorobenzaldehyde) in 175 mL of ethanol containing 700 mg of 10 percent palladium in charcoal is hydrogenated in a Parr hydrogenator for 4 hours, filtered, and concentrated at reduced pressure to an oil which is distilled to afford 31 g of the product of Formula F with a b.p. 150°–156° C./0.05 mm.

PREPARATIVE EXAMPLE 7

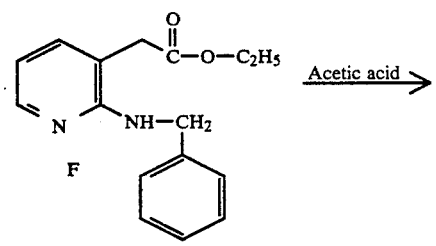

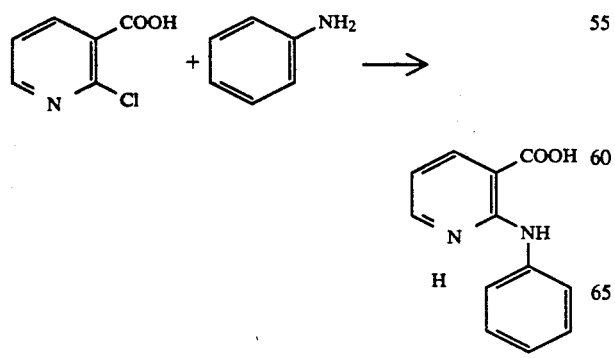

A solution of 30.7 g (0.114 m) of ethyl 2-(phenylmethyl-amino)-3-pyridineacetate (Formula F) in 250 mL of glacial acetic acid is heated at reflux for 1 hr. and then concentrated at reduced pressure. The resulting solid residue is recrystallized with ether to afford 19.1 g (m.p. 105°–106° C.) of the product of Formula G.

PREPARATIVE EXAMPLE 8

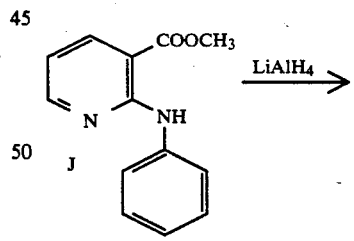

A stirred mixture of 118 g (0.75 mole) of 2-chloro-3-pyridinecarboxylic acid, 140 g (1.5 mole) of aniline, and 11.8 g of p-toluenesulfonic acid in 355 mL of water is heated at reflux for 8 hours. The precipitated product of Formula H is filtered and recrystallized with acetonitrile (125 g, m.p. 153°–155° C.).

PREPARATIVE EXAMPLE 9

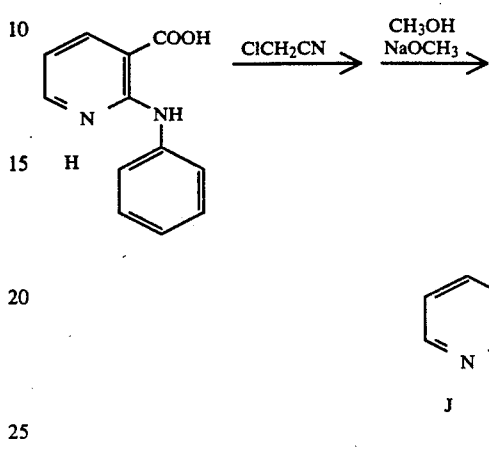

To a stirred solution of 71 g (0.33 mole) of 2-(phenylamino)-3-pyridinecarboxylic acid (Formula H) and 50 g of triethylamine in 500 mL of dry acetone is added 38 g (0.5 mole) of chloroacetonitrile. The reaction mixture is heated at reflux for 20 hours, filtered and concentrated under reduced pressure to a solid residue. The solid residue is mixed with 600 mg of sodium methoxide and dissolved in 800 mL of dry methanol, and heated at reflux for 3 hours, concentrated under reduced pressure, dissolved in ether and washed with water. The ether solution is dried over anhydrous MgSO4 and concentrated to an oil which is distilled and collected to yield 57 g of the product of Formula J, b.p. 158°–162° C.

PREPARATIVE EXAMPLE 10

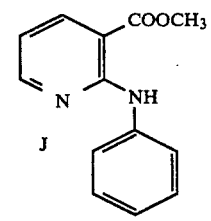

To a stirred suspension of 25 g (0.7 mole) of lithium aluminum hydride in 1300 mL of anhydrous ether is added 100 g (0.47 mole) of methyl 2-(phenylamino)-3-pyridin-carboxylate (Formula J) in 200 mL of ether for 1 hour. The mixture is heated at reflux for 20 hours, decomposed with 35 mL of water and 25 mL of 15 percent sodium hydroxide (NaOH) and filtered. Concentration of the filtrate affords 93 g syrup product of Formula K which forms the hydrogen bromide salt in 25 percent hydrogen bromide in ethanol (m.p. 172°–173° C.).

PREPARATIVE EXAMPLE 11

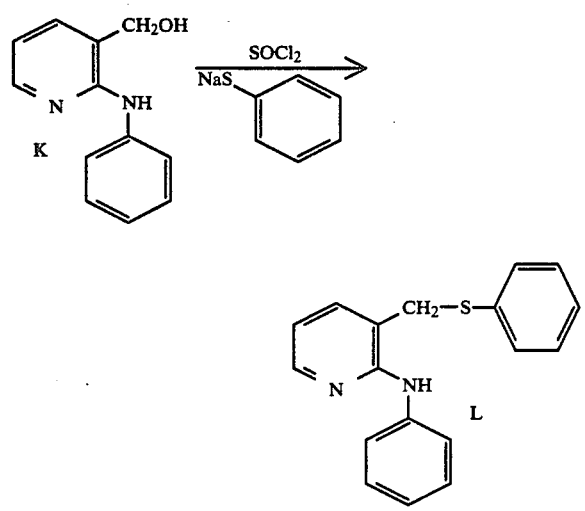

A sample of 25.5 g (0.108 mole) of 2-(phenylamino)-3-pyridine-methanol (Formula K) in 300 mL of dry methylene chloride is mixed with 22 mL of thionyl chloride and stirred at room temperature for 2 days. The precipitate is isolated by filtration, and added portionwise to a stirred sodium thiophenolate solution (10 g of thiophenol dissolved in 200 mL of ethanol and 8.4 g of sodium hydroxide in 20 mL of water). The solution is diluted with 100 mL water and the precipitated product is filtered to yield 21.9 g of product of Formula L, m.p. 65°–66° C.

PREPARATIVE EXAMPLE 12

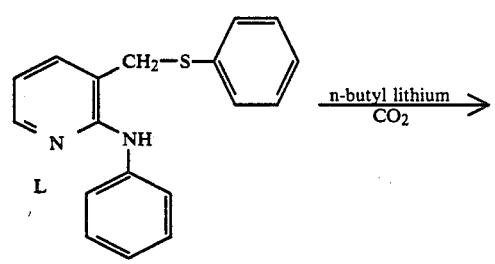

To a stirred solution of 50 g (0.171 mole) of 2-(phenylamino)-3-(phenylthiomethyl)-pyridine (Formula L) in 500 mL of dry tetrahydrofuran (THF) at −70° C. is added 0.43 mole of n-butyl-lithium-hexane solution. The reaction mixture is kept at 0° C. for 4 hours and poured onto 2000 mL of dry ice powder. Solvent is removed at reduced pressure and water (800 mL) is added to dissolve the residue. After washing with diethyl ether, the aqueous solution is neutralized with 15% hydrochloric acid and extracted with methylene chloride to yield 36 g of product of Formula M, m.p. 165°–166° C.

PREPARATIVE EXAMPLE 13

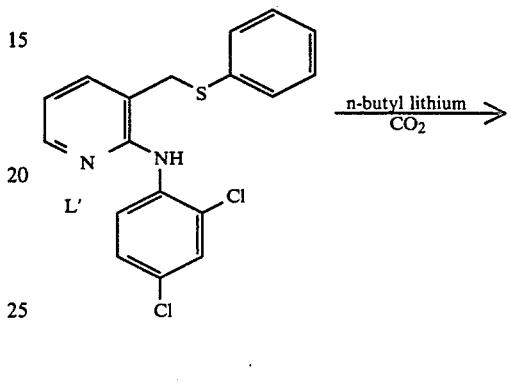

To a stirred solution of 11 g (0.03 mole) of 2-(2,4-dichlorophenylamino)-3-(phenylthiomethyl)-pyridine (Formula L' prepared as in Preparative Examples 8–11 starting with 2,4-dichloroaniline) in 100 mL of dry tetrahydrofuran (THF) at −70° C. is added 0.075 mole of n-butyl-lithium-hexane solution. The reaction mixture is kept at 0° for 4 hours and poured onto dry ice powder. Water is added at room temperature. After washing with ether, the aqueous solution is acidified with glacial acetic acid and the precipitated product is isolated by filtration to yield 4.6 g of compound of Formula N, m.p. 155°–156° C.

PREPARATIVE EXAMPLE 14

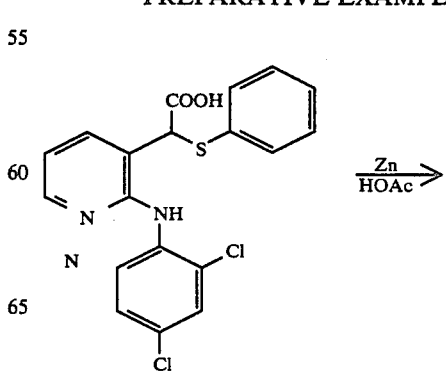

-continued

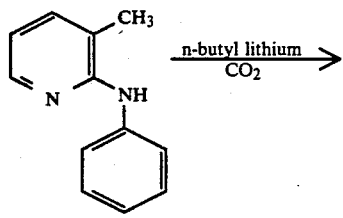

To a stirred solution of 4.6 g (0.0114 mole) of 2-(2,4-dichlorophenylamino)-α-phenylthio-3-pyridino-3-pyridineacetic acid (Formula N) in 100 mL of glacial acetic acid is added 3.7 g of zinc powder. After being stirred at room temperature for 2 days, the reaction mixture is heated at reflux for 1 hour, cooled, filtered, and concentrated at reduced pressure to afford the crude product which is purified by recrystallized with ether to yield 3 g of compound of Formula P, m.p. 184°–185° C.

PREPARATIVE EXAMPLE 15

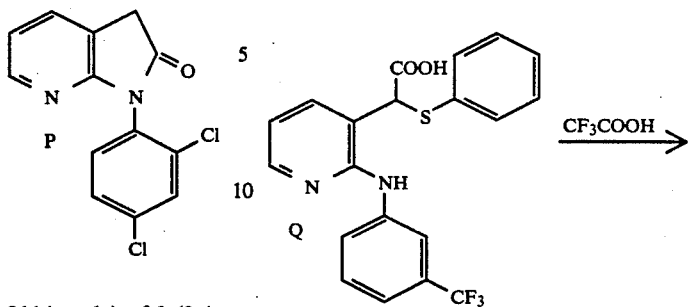

To a stirred solution of 10 g (0.054 mole) of 3-methyl-N-phenyl-2-pyridinamine in 220 mL of dry tetrahydrofuran at −10° C. is added 0.114 mole of n-butyl-lithium-hexane solution. After being kept at 0° for 4 hours, the reaction mixture is poured onto dry ice powder (1000 mL) and concentrated at room temperature under reduced pressure. The solid residue is triturated with ether, filtered, dissolved in 26 percent hydrogen chloride in ethanol, and heated at reflux for 10 minutes. Concentration affords 0.24 g of compound of Formula P', m.p. 118°–120° C.

PREPARATIVE EXAMPLE 16

To a stirred suspension of 5.6 g (0.0138 mole) of α-phenylthio-2-(3-trifluoromethylphenylamino)-3-pyridineacetic acid (Formula Q—which was prepared essentially ad described in Preparative Examples 8–11 and 13 by substituting 3-trifluoromethylaniline for aniline in Preparative Example 8) in 25 mL of methylene chloride is added 25 mL of trifluoroacetic acid. The mixture is stirred and kept at room temperature for 2 days and then concentrated in vacuo and purified by recrystallization with ether-petroleum ether to give 4.15 g of the compound of Formula R, m.p. 85°–87° C.

PREPARATIVE EXAMPLE 17

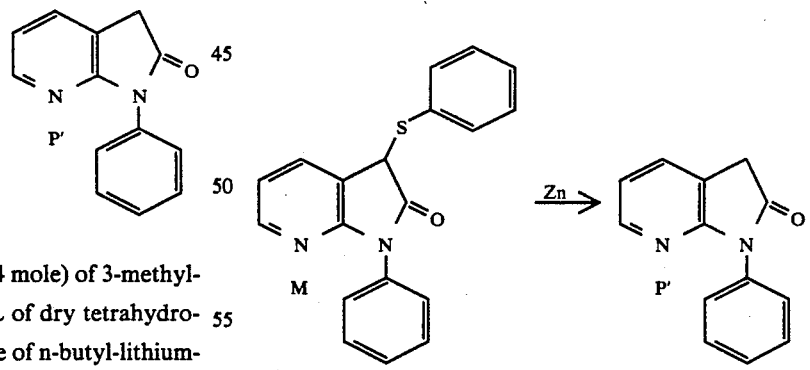

To a stirred solution of 47 g (0.148 mole) of 1,3-dihydro-1-phenyl-3-phenylthio-2H-pyrrolo-[2,3-b]-pyridin-2-one (Formula M) in 600 mL of THF is added 47 g of zinc powder followed by 78.5 g (0.723 mole) trimethylchlorosilane. The mixture is stirred at room temperature for 4 hours and filtered. The filtrate is diluted with ether, washed with water and 1N NaOH, dried over anhydrous $MgSO_4$, concentrated and purified by recrystallization with isopropyl ether/hexane to yield 18 g of the product of Formula P', m.p. 120°–121° C.).

PREPARATIVE EXAMPLE 18

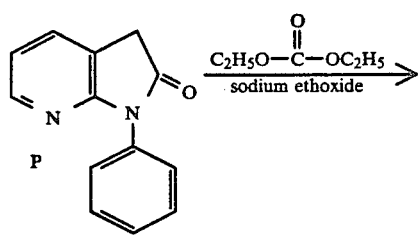

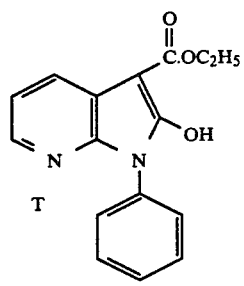

To a stirred solution of 0.022 mole of sodium ethoxide in 50 mL of dry ethanol is added 4.2 g (0.02 mole) of 1,3-dihydro-1-phenyl-2H-pyrrolo[2,3-b]-pyridin-2-one (Formula P) portionwise and followed 2.8 g (0.024 mole) of diethylcarbonate. The mixture is heated at reflux for 2 hours and then concentrated in reduced pressure. The residue is acidified with cold, dilute hydrochloric acid and extracted with ethyl acetate. Concentration of the organic extract followed by purification by recrystallization with ethanol yields 2.6 g of compound of Formula T, m.p. 130°–131° C.

By employing the procedures essentially as described above and employing the appropriate amine starting material for the group R, the following substituted 1,3-dihydro-2H-pyrrolo[2,3-b]pyridine-2-ones were prepared as listed in Table 2 below having the melting points listed in column 2.

TABLE 2

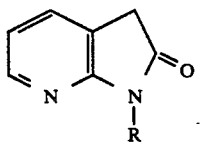

| Column 1 R | Column 2 Melting Point (°C.) | Methods of Preparation* |
|---|---|---|
| phenyl | 120–121 | a |
| 3-CF₃-phenyl | 132–134 | b |
| 4-Cl-phenyl | 154–155 | a, c |
| —CH₂-phenyl | 105–106 | d |
| —CH₂-⟨4-F-phenyl⟩ | 120–121 | e |
| —CH(CH₃)₂ | 65–66 | c |
| 4-CH(CH₃)₂-phenyl | 78–80 | a, c |
| 2,4-difluorophenyl | 128–129 | c, f |
| 4-methoxy-phenyl | 138–139 | a, c |
| 3,5-dichlorophenyl | 221–222 | c, f |

TABLE 2-continued

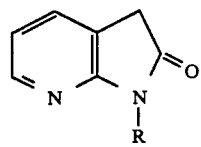

| Column 1 R | Column 2 Melting Point (°C.) | Methods of Preparation* |
|---|---|---|
| 2,4-dichlorophenyl | 184–185 | c, f |

*Compounds are synthesized according to
a: Preparative Example 1
b: Preparative Examples 8–11, 13, 16 and 17
c: Preparative Examples 8–12 and 17
d: Preparative Examples 4 and 5
e: Preparative Examples 6 and 7
f: Preparative Examples 8–11, 13 and 14

EXAMPLE 1

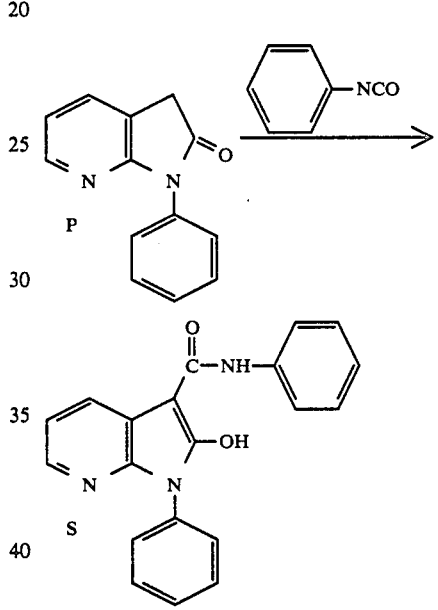

To a stirred solution of 6.3 g (0.03 mole) of 1,3-dihydro-1-phenyl-2H-pyrrolo[2,3-b]-pyridin-2-one (Formula P) in 100 mL of tetrahydrofuran is added 0.33 mole of 60 percent sodium hydride (in oil dispersion) and followed by 3.7 g (0.031 mole) of phenylisocyanate. The mixture is kept at room temperature for 4 hours and poured into ice water. Aqueous solution is separated, washed with ether, and acidified with 10 percent hydrochloric acid. The precipitated product is isolated by filtration and purified by recrystallization with acetonitrile to give 5.5 g of the compound of Formula S, m.p. 199°–200° C.

EXAMPLE 2

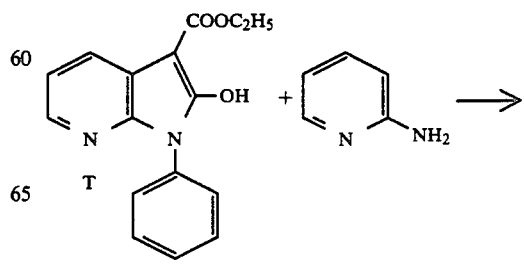

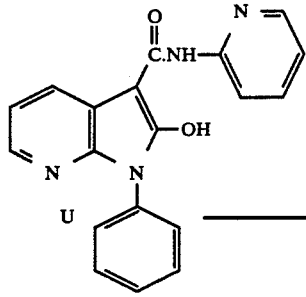

U methanol affords 1.4 g of the compound of Formula U, m.p. 243°–4° C.

By employing basically the same procedures as set forth in Examples 1 and 2 above and employing the appropriate isocyanate or amine starting material for the group $R^1$, the substituted 1H-pyrrolo[2,3-b]pyridine-3-carboxamides are prepared as listed in Table 3 below having the melting points listed in Column 3:

TABLE 3

| Column 1<br>R | Column 2<br>$R^1$ | Column 3<br>m.p. (°C.) | Method of<br>Preparation* |
|---|---|---|---|
| 3-$CF_3$-phenyl | phenyl | 191–192 | a |
| phenyl | 2,4-difluorophenyl | 210–212 | b |
| 4-chloro | phenyl | 224–225 | a |
| —$CH_2$-phenyl | phenyl | 188–189 | a |
| phenyl | (isoxazolyl-CH3 group) | 244–246 | b |
| H | phenyl | 300–302 | a |
| phenyl | —$SO_2$—C6H4—$CH_3$ | 237–240 | a |
| phenyl | 4-methoxyphenyl | 238–240 | a |
| phenyl | —$(CH_2)_3CH_3$ | 137–138 | a |
| phenyl | —$CH_2$-phenyl | 167–168 | a |
| —$CH_2$—C6H4—F | phenyl | 185–186 | a |
| —$CH(CH_3)_2$ | phenyl | 136–137 | a |
| phenyl | 3-COOH-4-OH-phenyl | 268–270 | b |
| phenyl | —$C(CH_3)_3$ | 195–197 | a |
| —C6H4—$CH(CH_3)_2$ | phenyl | 196–198 | a |
| methyl | phenyl | 155–157 | a |

*Prepared according to
a: Example 1
b: Example 2

60

A mixture of 2.82 g (0.01 mole) of ethyl 2-hydroxy-1-phenyl-1H-pyrrolo[2,3-b]-pyridine-3-carboxylate (Formula T) and 0.95 g (0.01 mole) of 2-aminopyridine in 70 mL of dry xylene is heated at reflux for 5 hours. Concentration and recrystallization of the solid residue from The following formulations exemplify some of the dosage forms of the compositions of this invention. In each, the term "active compound" refers to

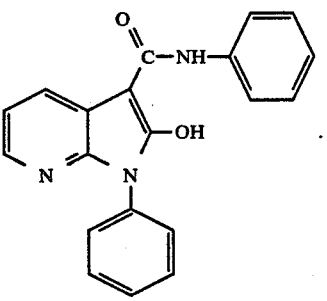

However, this compound may be replaced by equally effective amounts of other compounds of the invention.

EXAMPLE A

| Cream | |
|---|---|
| Ingredient | mg/g |
| Active Compound | 1.0–20.0 |
| Stearic Acid, USP | 60.0 |
| Glyceryl Monostearate | 100.0 |
| Propylene Glycol, USP | 50.0 |
| Polyethylene Sorbitan Monopalmitate | 50.0 |
| Sorbitol Solution, USP | 30.0 |
| Benzyl Alcohol, NF | 10.0 |
| Purified Water, USP to make | 1.0 g |

Method of Manufacture

Heat the stearic acid, glyceryl monostearate and polyethylene sorbitan monopalmitate to 70° C. In a separate vessel, dissolve sorbital solution, benzyl alcohol, water, and half quantity of propylene glycol and heat to 70° C. Add the aqueous phase to oil phase with high speed stirring. Dissolve the active compound in remaining quantity of propylene glycol and add to the above emulsion when the temperature of emulsion is 37°–40° C. Mix uniformly with stirring and cool to room temperature.

EXAMPLE B

| Lotion | |
|---|---|
| Ingredient | mg/g |
| Active Compound | 1.0–20.0 |
| Carbomer 940 | 3.0 |
| Sodium hydroxide (charged as 4% w/w) | 0.05 |
| Carbomer 940 | 3.0 |
| Sodium hydroxide (charged as 4% w/w aqueous solution) | 0.05 |
| Isopropyl Alcohol | 40.00 |
| Purified Water, USP to make | 1.0 g |

Method of Manufacture

Prepare a 4% solution of sodium hydroxide in water. Heat the purified water to 60° C. Add Carbomer ® 940 and mix at high speed until dispersed. Cool the above mixture to room temperature and slowly charge sodium hydroxide solution until uniform. Add 80% of isopropyl alcohol to the above with mixing. Dissolve the active compound in remaining isopropyl alcohol. Add this to the mixture with stirring. Adjust pH to 5.0 to 5.5 with sodium hydroxide, if necessary.

While the present invention has been described in conjunction with the specific embodiments set forth above, many alternatives, modifications and variations therefore will be apparent to those of ordinary skill in the art. All such alternatives, modifications and variations are intended to fall within the spirit and scope of the present invention.

What is claimed is:

1. A compound of the structural formula:

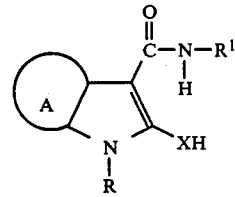

or a pharmaceutically acceptable salt or solvate thereof, wherein:

ring A represents a fused pyridine ring;

X is oxygen or sulfur;

R represents hydrogen, alkyl, aryl, aralkyl, or a heterocyclic aromatic group;

$R^1$ represents alkyl, aryl, aralkyl, or a heterocyclic aromatic group.

2. A compound according to claim 1, wherein ring A represents

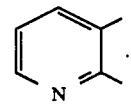

3. A compound according to claim 2, wherein X is O.

4. A compound according to claim 3, wherein $R^1$ represents alkyl, phenyl, substituted phenyl, 2-, 3- or 4-pyridyl, 2- or 3-furyl, 2- or 3-thienyl, 2-, 4- or 5-thiazolyl, 2- or 4-imidazolyl, 3-oxazolyl or 5-methyl-3-oxazolyl.

5. A compound according to claim 4, wherein R represents H, alkyl, phenyl or substituted phenyl.

6. A compound according to claim 3, wherein $R^1$ represents phenyl or substituted phenyl.

7. A compound according to claim 6, wherein R represents phenyl or substituted phenyl.

8. A compound according to claim 1 of the formula:

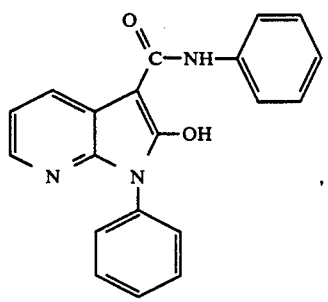

-continued

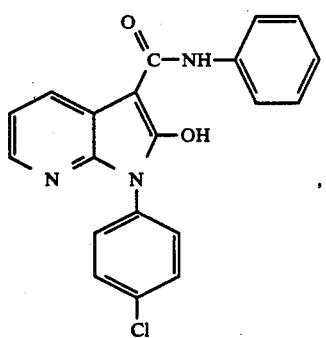

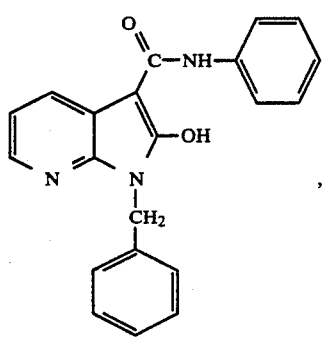

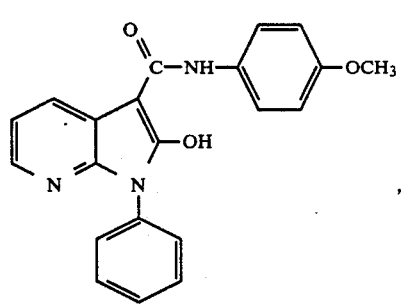

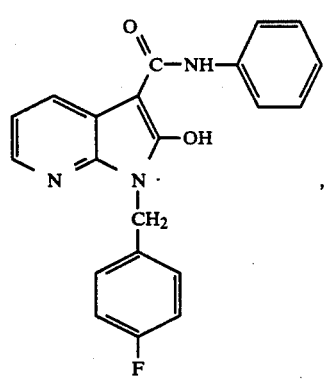

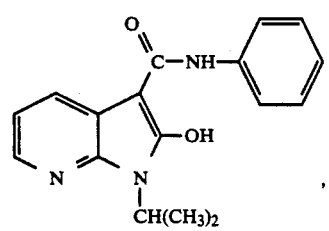

-continued

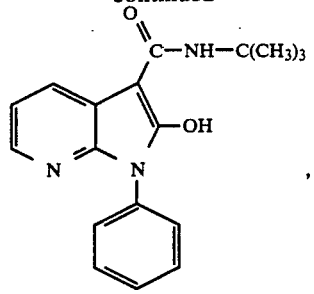

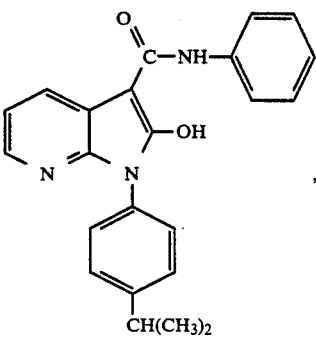

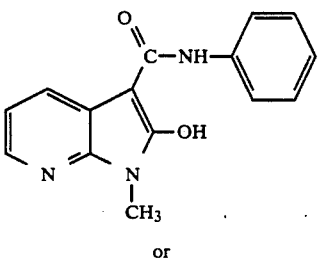

or

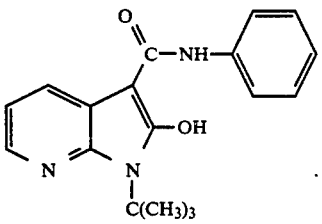

9. A compound according to claim 1 of the formula:

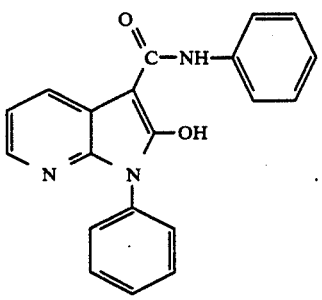

10. A pharmaceutical composition comprising a compound of formula I as defined in claim 1 in combination with a pharmaceutically acceptable carrier.

11. A method for treating inflammation in a mammal comprising administering to said mammal an anti-inflammatory effective amount of a compound of formula I as defined in claim 1.

* * * * *

UNITED STATES PATENT AND TRADEMARK OFFICE
CERTIFICATE OF CORRECTION

PATENT NO. : 5,023,265
DATED : June 11, 1991
INVENTOR(S) : Sherlock, et al.

It is certified that error appears in the above-identified patent and that said Letters Patent is hereby corrected as shown below:

On the cover page, immediately below "United States Patent", "Scherlock" should read --Sherlock--.

Also on the cover page, after "[75] Inventors:", "Margaret H. Scherlock" should read --Margaret H. Sherlock--.

Signed and Sealed this

Twenty-third Day of May, 1995

Attest:

BRUCE LEHMAN

Attesting Officer     Commissioner of Patents and Trademarks